United States Patent [19]
Venturelli

[11] Patent Number: 6,007,545
[45] Date of Patent: Dec. 28, 1999

[54] DILATING CATHETER FOR THE INTRODUCTION OF EXPANDABLE STENTS

[75] Inventor: Andrea Venturelli, Concesio, Italy

[73] Assignee: Invatec S.r.l., Concesio (Brescia), Italy

[21] Appl. No.: 09/063,155

[22] Filed: Apr. 20, 1998

[30] Foreign Application Priority Data

Sep. 12, 1997 [IT] Italy ................................. BS97U0097

[51] Int. Cl.⁶ ..................................................... A61F 11/00
[52] U.S. Cl. .............................. 606/108; 606/194; 623/1; 623/9
[58] Field of Search .................... 606/108, 194; 623/1, 9; 604/30

[56] References Cited

U.S. PATENT DOCUMENTS

| | | | |
|---|---|---|---|
| 4,969,458 | 11/1990 | Wiktor | 606/194 |
| 5,197,948 | 3/1993 | Ghodsian | 604/30 |
| 5,409,495 | 4/1995 | Osborn | 606/108 |
| 5,522,882 | 6/1996 | Gaterud et al. | 606/108 |
| 5,545,209 | 8/1996 | Roberts et al. | 606/108 |
| 5,645,560 | 7/1997 | Crocker et al. | 606/108 |
| 5,653,689 | 8/1997 | Buelna et al. | 606/108 |
| 5,693,066 | 12/1997 | Rupp et al. | 606/198 |
| 5,849,035 | 12/1998 | Pathak et al. | 606/108 |

*Primary Examiner*—Michael Buiz
*Assistant Examiner*—(Jackie) Tan-Uyen T. Ho
*Attorney, Agent, or Firm*—McGlew and Tuttle, P.C.

[57] ABSTRACT

A dilating catheter is provided for introducing and inserting an expandable stent. The dilating catheter includes an inflatable balloon, which is applied on a distal section of said catheter and which can be wrapped, if empty, on the section in order to be applied there around a the contracted stent. The outer surface of the balloon is roughened by means of a supply of material or a deformation in order to offer greater interference and grip to the said stent contracted tightly around it.

19 Claims, 1 Drawing Sheet

DILATING CATHETER FOR THE INTRODUCTION OF EXPANDABLE STENTS

FIELD OF THE INVENTION

The present invention pertains to the instruments for the introduction and the mechanical dilation of stents in the ducts or lumina of a live, either human or animal body.

BACKGROUND OF THE INVENTION

Stents are tubular molds which are made of biocompatible materials and are contracted upon their introduction and then they dilate for their insertion into the desired duct or lumen. Some types of stents dilate mechanically, and they require for their insertion the use of an expandable element arranged along the introducing instrument and dilatable inside the stent.

As the instrument for the introduction of mechanically dilating stents, a catheter having an inflatable balloon at its distal end of the type already used may be used, e.g., for the dilation of arterial ducts or other lumina in a live body. Therefore, for the introduction operation, the balloon, empty, is wrapped tightly around a corresponding zone of the catheter, and the stent, in its turn, is arranged tightly around the balloon in order to remain fixed there during the introduction into a lumen.

However the requirements of a catheter for the simple dilation of ducts or lumina most often are incompatible with those of a catheter for the positioning of a stent, which is why specific catheters would be needed for one or the other operation.

A dilating catheter, for example, for angioplasty procedures, or the like, must have a small diameter, a highly resistant balloon, and a low coefficient of surface friction. On the other hand a catheter for positioning stents must have a remarkable friction at least at the balloon, must be made of a material with a moldable surface that is adapted to the interior of the closed, i.e., contracted stent, and must have a diameter of the balloon, when closed around the catheter, at least slightly greater than the internal diameter of the closed stent. All this is to interfere with the stent and to hold it, preventing its loss during the insertion in a duct or lumen.

In other words, the surface slipperiness of the balloon may be a cause of a loss of the stent.

In addition, a diameter in the zone of the catheter, including the closed balloon wrapped there, that is smaller than the internal diameter of the closed stent that is applied there may cause:

a so-called overlapping resulting from a corrugation and an overlapping of some parts of the stent with possible deformation of its structure, if the stent is contracted too tightly in order to make it adhere to such a zone; or an improper fixation of the stent with the possibility still of losing it during the introduction if the stent, although suitably and correctly closed, does not adhere to the outer surface of the catheter plus closed balloon.

SUMMARY AND OBJECTS OF THE INVENTION

Starting from these representative premises of the state of the art, the object of the present invention is to provide a valid solution to the problems mentioned above and to correspondingly provide a dilating catheter improved at the level of the inflatable balloon, so that this constitutes a valid, positive grip to interfere with and to hold the stent that is applied there from inside, so as to prevent the loss of the latter during the introduction phase without, however, having an effect on the dilatability of the balloon when the stent is expanded and released.

According to the invention, a dilating catheter is provided for introducing and inserting an expandable stent. The dilating catheter includes an inflatable balloon, which is applied on a distal section of said catheter and which can be wrapped, if empty, on the section in order to be applied there around a the contracted stent. The outer surface of the balloon is roughened by means of a supply of material or a deformation in order to offer greater interference and grip to the said stent contracted tightly around it.

In practice, the outer surface of the balloon is roughened with a material coating having a higher coefficient of friction and through a deformation or an embossing of the wall of the said balloon for an increase in the friction and/or diameter of the balloon, and so that the stent is in a better anchoring position when it is in its contracted position around the balloon.

Greater details of the present invention will become more evident from the description given below with reference to the attached drawings.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENT

Figure 1:
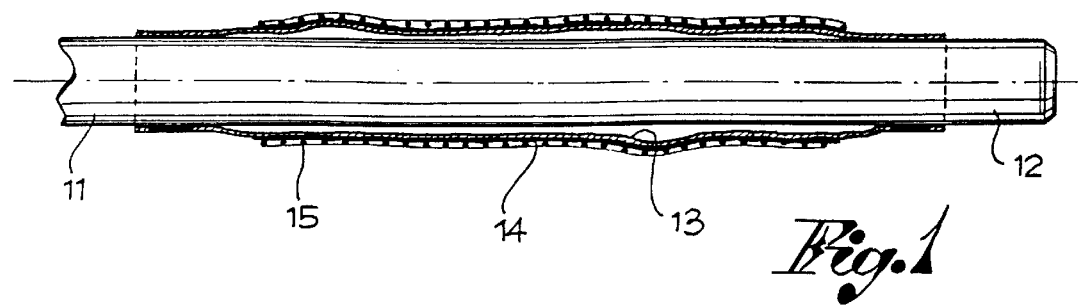
FIG. 1 is a partial sectional view showing a part of a catheter with balloon modified according to the present invention and with a stent contracted around the empty balloon.

Referring to the drawings in particular, a catheter element is indicated globally by 11 and has, in the known manner, an inflatable balloon 13 on its distal section 12.

Figure 2:
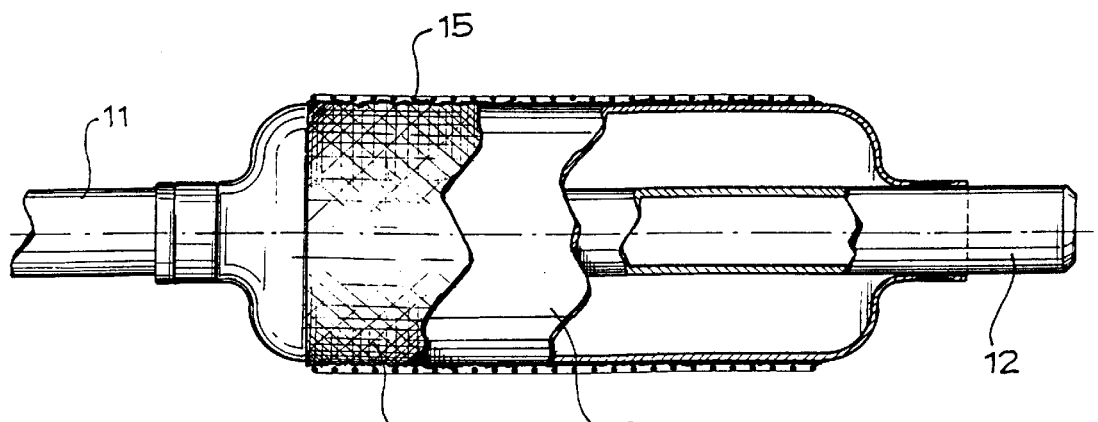
FIG. 2 is a similar view of the catheter of FIG. 1, but with the balloon and stent expanded.

According to the present invention and according to a first embodiment as shown in FIGS. 1 and 2, a layer 14 of a material having a high coefficient of friction or of roughening of this surface is coated on the outer surface of the balloon 13, for at least a section of its length. The material for the formation of this surface layer 14 may be a silicone, gel, or other biocompatible product that is chemically bound by vulcanization or by another suitable method with the material that forms the balloon. Therefore, the coated layer 14 contributes to an increase in the external diameter of the balloon for its greater interference with the inside of a stent 15, which is tightly provided around it, and moreover, increases the surface friction of the balloon in order to better hold the stent against the longitudinal sliding and therefore against the loss during the introduction in a duct or lumen.

Figure 3:
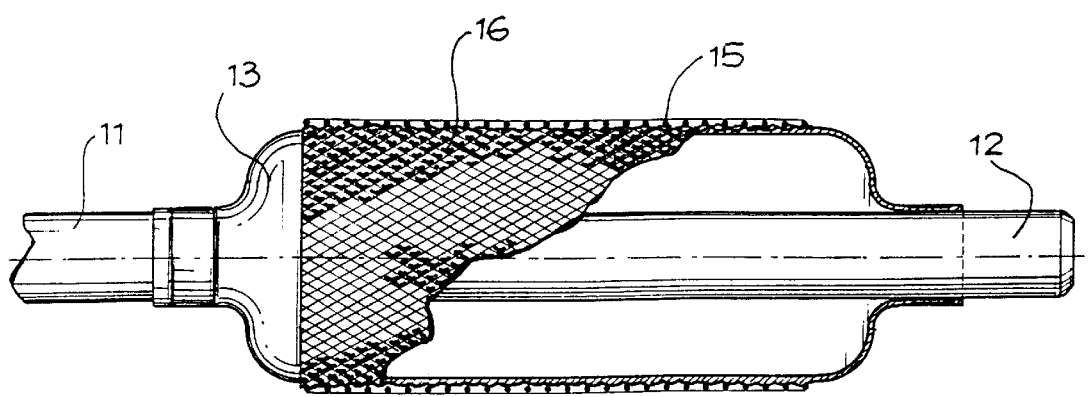
FIG. 3 is a view similar to FIG. 2, but showing another way of roughening the outer surface of the balloon.

A similar result can be achieved without the coating of a material on the outer surface of the balloon but by means of a deformation or corrugation of the wall of the balloon, e.g., by means of knurling or embossing 16 as shown in FIG. 3.

FIG. 1 shows the condition of the balloon, which is empty and is wrapped around the catheter, and the stent, which is contracted around the same, while FIGS. 2 and 3 show the condition of expansion of the balloon and the dilation of the stent for the release of same, when the balloon has an outer coated layer and a corrugated wall, respectively.

While specific embodiments of the invention have been shown and described in detail to illustrate the application of the principles of the invention, it will be understood that the invention may be embodied otherwise without departing from such principles.

What is claimed is:

1. A dilating catheter for introducing and inserting an expandable stent, the dilating catheter comprising:
    a catheter element;
    an inflatable balloon, which is applied on a distal section of said catheter element and which can be wrapped, when empty, on said distal section in order to be applied with a contracted stent there around, said balloon having an outer surface with a roughened portion providing greater interference and grip with the stent contracted tightly around it, said roughened portion being formed by one of a material applied on said balloon and a deformation of said balloon.

2. The dilating catheter in accordance with claim 1, wherein an outer layer of said material has a high coefficient of friction, said layer of material being chemically bound by vulcanization or by another method with said balloon to be coated.

3. The dilating catheter in accordance with claim 2, wherein said layer of material increases an external diameter and a surface friction of said balloon.

4. The dilating catheter in accordance with claim 3, wherein said material is a silicone, a gel or another biocompatible product.

5. The dilating catheter in accordance with claim 1, wherein a wall of said balloon is deformed in order to have corrugations, knurling, or embossing for interfering with the stent applied thereto.

6. A dilating catheter for introducing and inserting an expandable stent, the dilating catheter comprising:
    a catheter element;
    an inflatable balloon, which is applied on a distal section of said catheter element and which can be wrapped, when empty, on said distal section in order to be applied with a contracted stent there around, said balloon having an outer surface having a friction with the stent for fastening the stent to said balloon during insertion of said catheter element into a patient.

7. The dilating catheter in accordance with claim 6, wherein said roughened portion is formed by a material layer applied on said balloon, said material layer having a high coefficient of friction.

8. The dilating catheter in accordance with claim 7, wherein said material layer is chemically bound by vulcanization or by another method with said balloon to be coated.

9. The dilating catheter in accordance with claim 7, wherein said material layer increases the external diameter and the surface friction of said balloon.

10. The dilating catheter in accordance with claim 8, wherein said material layer is a silicone, a gel or another biocompatible product.

11. The dilating catheter in accordance with claim 6, wherein said roughened portion is formed by a deformation of said balloon wherein a wall of said balloon is deformed to provide at least one of corrugations, knurling, and embossing for interfering with the stent applied thereto.

12. The catheter in accordance with claim 1, wherein:
    said roughened portion has friction with said stent for fastening the stent to said balloon during insertion of the catheter into a patient.

13. The catheter in accordance with claim 6, wherein:
    said friction includes a roughened portion on said outer surface of said balloon.

14. A stent delivery system comprising:
    a catheter;
    a stent arranged around said catheter;
    a balloon arranged on said catheter between said catheter and said stent, an outer surface of said balloon having friction means with said stent for fastening said stent to said balloon during insertion of said catheter into a patient, said friction means includes a roughened portion on said outer surface of said balloon.

15. The system in accordance with claim 14, wherein:
    said roughened portion is formed by a material layer applied on said balloon, said material layer having a high coefficient of friction.

16. The system in accordance with claim 14, wherein:
    said roughened portion is formed by a deformation of said outer surface of said balloon.

17. The system in accordance with claim 16, wherein:
    said deformation includes one of corrugations, knurling, and embossing for interfering with said stent.

18. The system in accordance with claim 14, wherein:
    said balloon is inflatable from a compact state to an expanded state,
    said friction means exists during said compact state of said balloon.

19. The system in accordance with claim 14, wherein:
    said stent is expandable between a compact state and an expanded state;
    said balloon is inflatable from a compact state to an expanded state and is adjacent said catheter and said stent when said catheter and said stent are in said compacted state.

* * * * *